(12) United States Patent
Romano et al.

(10) Patent No.: US 8,905,949 B2
(45) Date of Patent: Dec. 9, 2014

(54) DEVICE FOR OCULAR ULTRASOUND THERAPY HAVING A REFLECTOR

(75) Inventors: Fabrizio Romano, Beynost (FR);
Thomas Charrel, Lyons (FR); Cyril Lafon, Toussieu (FR); Philippe Chapuis, Pommiers (FR); Jean-Yves Chapelon, Villeurbanne (FR)

(73) Assignee: Eye Tech Care, Paris (FR)

( * ) Notice: Subject to any disclaimer, the term of this patent is extended or adjusted under 35 U.S.C. 154(b) by 0 days.

(21) Appl. No.: 14/009,622

(22) PCT Filed: Apr. 5, 2012

(86) PCT No.: PCT/EP2012/056254
§ 371 (c)(1),
(2), (4) Date: Oct. 3, 2013

(87) PCT Pub. No.: WO2012/136752
PCT Pub. Date: Oct. 11, 2012

(65) Prior Publication Data
US 2014/0025098 A1  Jan. 23, 2014

(30) Foreign Application Priority Data
Apr. 5, 2011 (FR) ........................ 11 52933

(51) Int. Cl.
| | |
|---|---|
| *A61H 1/00* | (2006.01) |
| *A61H 1/02* | (2006.01) |
| *A61H 5/00* | (2006.01) |
| *A61F 9/007* | (2006.01) |
| *A61N 7/02* | (2006.01) |
| *A61N 7/00* | (2006.01) |

(52) U.S. Cl.
CPC ...... *A61F 9/00781* (2013.01); *A61N 2007/0069* (2013.01); *A61N 2007/0065* (2013.01); *A61F 9/007* (2013.01); *A61N 7/02* (2013.01)
USPC ................................. 601/2; 600/437

(58) Field of Classification Search
None
See application file for complete search history.

(56) References Cited

U.S. PATENT DOCUMENTS

| | | | |
|---|---|---|---|
| 4,484,569 | A | 11/1984 | Driller et al. |
| 5,230,334 | A | 7/1993 | Klopotek |
| 2011/0009779 | A1 | 1/2011 | Romano et al. |
| 2011/0301507 | A1 | 12/2011 | Romano et al. |
| 2012/0136281 | A1 | 5/2012 | Romano et al. |

FOREIGN PATENT DOCUMENTS

| | | |
|---|---|---|
| DE | 4430720 | 6/1995 |
| WO | 02/38078 | 5/2002 |
| WO | 2009/103721 | 8/2009 |
| WO | 2011/020495 | 2/2011 |

OTHER PUBLICATIONS

International Search Report for PCT/EP2012/056254 Mailed July 20, 2012.

*Primary Examiner* — Joel Lamprecht
(74) *Attorney, Agent, or Firm* — Miles and Stockbridge

(57) ABSTRACT

The present invention relates to a device for treating an ocular pathology, including a ring (1) comprising a proximal end intended to be in contact with an eye of a patient, and a distal end intended to receive ultrasound generating means (2), wherein the device additionally includes at least one reflector (3) for reflecting and focusing ultrasound generated by the generation means.

12 Claims, 4 Drawing Sheets

US 8,905,949 B2

DEVICE FOR OCULAR ULTRASOUND THERAPY HAVING A REFLECTOR

CROSS REFERENCE TO RELATED APPLICATION

This application is a §371 National Stage Application of PCT/EP2012/056254, filed Apr. 5, 2012, and claims priority to French Application No. 1152933, filed Apr. 5,2011.

BACKGROUND OF THE INVENTION

1. Field of the Invention

The present invention concerns the general technical field of non-invasive treatment of an ocular pathology.

It more specifically concerns a device and method for generating focused, planar or unfocused ultrasound of high or low intensity for the treatment of an ocular pathology such as glaucoma.

2. Description of Related Art

Glaucoma is an optical neuropathy i.e. a disorder of the optical nerve due to high intraocular pressure (IOP).

The eye is a hollow structure composed of two segments: the anterior segment between the cornea and crystalline lens, and the posterior segment between the crystalline lens and the retina. The anterior segment contains a transparent liquid called "aqueous humour".

The aqueous humour is formed in the posterior chamber of the eye's anterior segment by the ciliary body. The liquid which is generated at a relatively constant rate then passes around the crystalline lens through the pupil opening in the iris and into the anterior chamber of the eye. The aqueous humour is then evacuated through the trabeculum and Schlemm's canal.

When the aqueous humour is no longer evacuated sufficiently rapidly it builds up leading to a rise in IOP. An increase in IOP compresses the axons in the optic nerve and may also compromise the vascularisation of the optic nerve. High IOP over a long period may cause total loss of vision.

The sole therapeutic approach currently available to treat glaucoma consists of reducing intraocular pressure:

either by improving drainage of aqueous humour;
or by reducing the production of aqueous humour.

Different devices are known for reducing the production of aqueous humour based on the principle of cyclophotocoagulation. Documents DE 44 30 720 and WO 02/38078 describe devices each comprising an applicator generating energy for burning a spot region of the ciliary body so that the ciliary body produces less aqueous humour. The user positions the applicator on the white part of the eye in contact with the sclera at an angle of incidence perpendicular to the surface of the eye. The user then generates a laser burst in order to burn the spot region of the ciliary body. The applicator is then moved by the user in order to burn a following spot of the ciliary body.

One disadvantage with these devices is that they only allow one spot region of the ciliary body to be treated at one time, which means that it is necessary to repeat the applicator positioning operations and to apply the laser a plurality of times to treat the entire circumference of the eye. This repeating of positioning and laser application operations increases surgery time and the risk of error.

To overcome these disadvantages document WO 2009/103721 particularly proposes a device for treating an ocular pathology comprising a ring having a proximal portion suitable to be in contact with the eye and a distal portion suitable to receive means for generating high intensity focused ultrasound beam. The means for generating ultrasound comprise six transducers having a concave profile in the form of cylinder segments positioned on a cylindrical supporting ring.

With this device it is possible to treat glaucoma in a single step. However the manufacturing of means to generate high intensity focused ultrasound beam of and in particular the positioning of the transducers on the cylindrical support may be difficult to implement.

An aim of the present invention is to propose an easier device to manufacture than the device described in WO 2009/103721.

SUMMARY

To this end, the invention proposes a device for treating ocular pathology comprising a ring having a proximal end suitable to be in contact with a patient's eye and a distal end suitable to receive ultrasound generating means, wherein the device further comprises a reflector including an active concave surface facing the ultrasound generating means to reflect and focus the ultrasound generated by the generating means in a region of the patient's eye.

DETAILED DESCRIPTION OF THE PREFERRED EMBODIMENT

Preferred but non-limiting aspects of the device of the invention are the following:

each reflector comprises an active concave face facing the ultrasound generating means to reflect and focus the ultrasound waves in a region of the patient's eye;

the ultrasound generating means comprise at least one transducer having a front face to radiate ultrasound, the front face of each transducer extending parallel to the axis of revolution of the ring;

the ultrasound generating means comprise a single tubular transducer;

the ultrasound generating means comprise a plurality of transducers, said transducers being positioned on the generating lines of a tube;

each transducer is in the form of a cylinder portion;

each transducer is planar;

the device further comprises a support for supporting the ultrasound generating means and each reflector, the ultrasound generating means being positioned in a central region of the support and each reflector being positioned in a peripheral region of the support;

the reflector comprises an active toroid concave face;

the reflector comprises a plurality of reflection elements, each reflection element comprising an active face in the form of a cylinder portion;

the device further comprises a support for supporting the ultrasound generating means and each reflector, the ultrasound generating means being positioned in a peripheral region of the support and each reflector being positioned in a central region of the support;

the reflector comprises an active face in the form of a concave or planar or convex truncated cone;

the ultrasound generating means are of tubular shape and the reflector is of concave, planar or convex truncated cone shape, the diameter of the tubular generating means being larger than the diameter of the reflector, the ultrasound generating means and the reflector being arranged so that:

the axes of revolution of the reflector and of the ultrasound generating means merge;

the ultrasound generating means surround the reflector;

the inner side of the ultrasound tubular generating means radiating the ultrasound waves lies opposite to the active face of the reflector.

Other advantages and characteristics will become better apparent from the following description of several variants of embodiment given as non-limiting examples referring to the appended drawings in which FIGS. 1 to 4 illustrate different variants of the device of the invention.

Figure 1:
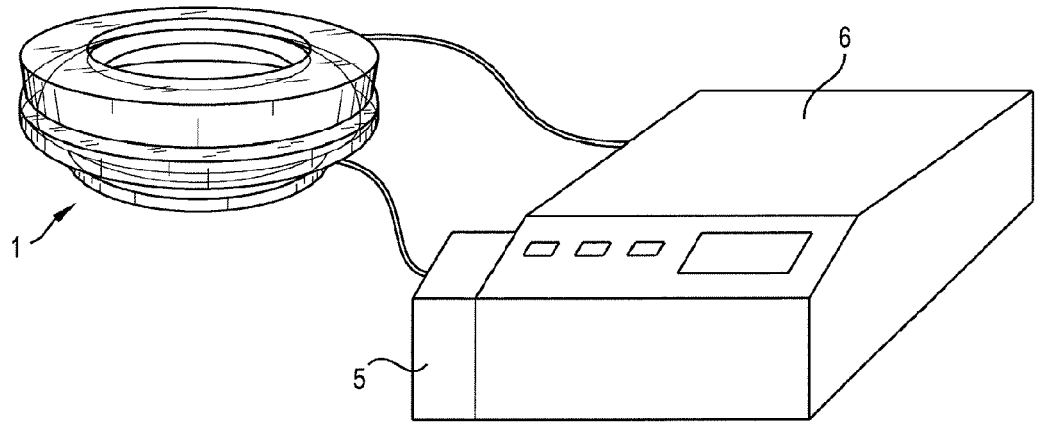
FIGS. 1-4, 6, and 7 illustrate different variants of the device of the invention.
Figure 2:
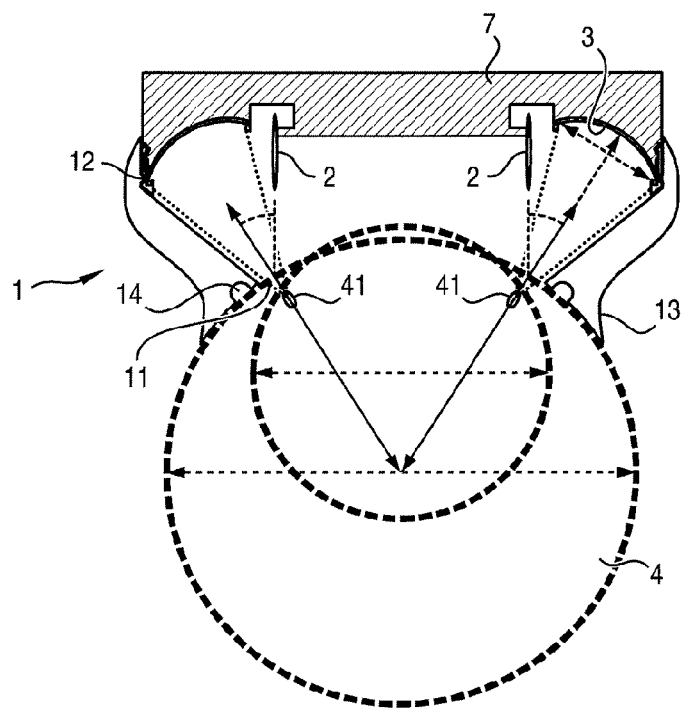

With reference to FIGS. 1 and 2 one embodiment is illustrated of the device for treating an ocular pathology.

The device comprises:

a ring 1;

ultrasound generating means 2 to generate ultrasound; and a reflector 3 to reflect, direct and focus the ultrasound waves emitted by the ultrasound generating means 2.

Ring

The ring 1 is a truncated cone open at both ends. The small base 11 of the truncated cone forms the proximal end of the ring 1, and the large base 12 forms the distal end of the ring 1.

The proximal end 11 is intended to come into contact with a patient's eye 4. The distal end 12 of the ring 1 is intended to receive the ultrasound generating means 2.

With reference to FIG. 1, the proximal end 11 of the cone comprises an outer annular flange 13 suitable to be applied onto the outer surface of the eye 4, at about 2 mm away from the limbus, the limbus being the junction between the cornea and the sclera.

The proximal edge 11 of the cone also comprises annular groove 14 connected to a suction device 5 via at least one opening passing through the cone 1 and leading into the annular groove 14. Advantageously, the suction device 5 can be controlled by a control unit 6.

Evidently the suction device 5 may be independent without departing from the scope of the invention.

The operating principle of the suction device 5 is as follows. The cone 1 is applied to the patient's eye 4 and the suction device 5 is actuated. This sets up a vacuum in the annular groove 14 which causes deformation of the conjunctiva of the eye 4, this deformation forming a toroid seal in the annular groove 14.

The cone 1 is then closely joined to the eye 4 so that the cone 1 will follow the micro-movements of the eye 4 throughout the duration of treatment. This allows the ensured maintaining of the position of the apparatus centred on the visual axis.

The constituent material of the ring 1 may be medical grade silicon. This material firstly has the advantage of being flexible and secondly the advantage of being compatible with conjunctival contact. However, the cone 1 may evidently be formed of any biocompatible material known to the skilled person such as biocompatible PVC.

Ultrasound Generating Means:

The ultrasound generating means 2 allow the generating of ultrasound energy.

The associating of the generating means 2 with the reflector 3 allows a high intensity focused ultrasound source to be obtained.

The ultrasound generating means 2 are connected to the control unit 6. This unit comprises a burst generator and means for specifying the burst parameters such as frequency, power and duration of each burst, etc.

The burst generator comprises at least one sinusoid signal generator at a determined frequency between 5 and 35 MHz, preferably between 10 and 25 MHz, an amplifier and an electric counter.

Reflector

The reflector 3 is used to reflect the ultrasound waves generated by the ultrasound generating means 2.

The reflector 3 comprises a concave face—called "active face"—to direct and focus the ultrasound waves generated by the ultrasound generating means 2 into a region of the eye 4, and in particular into the region of the ciliary body 41 of the eye 4. More specifically, each point on the active concave face is calculated iteratively following Snell-Descartes law so that the ultrasound waves reflected by said active face are focused in the region of the ciliary body 41.

The reflector 3 is in a material allowing the reflecting of ultrasound waves, such as brass.

Examples of Embodiment

A description will now be given of different embodiments of the device for treating an ocular pathology using HIFU.

Prototype 1

Figure 3A:
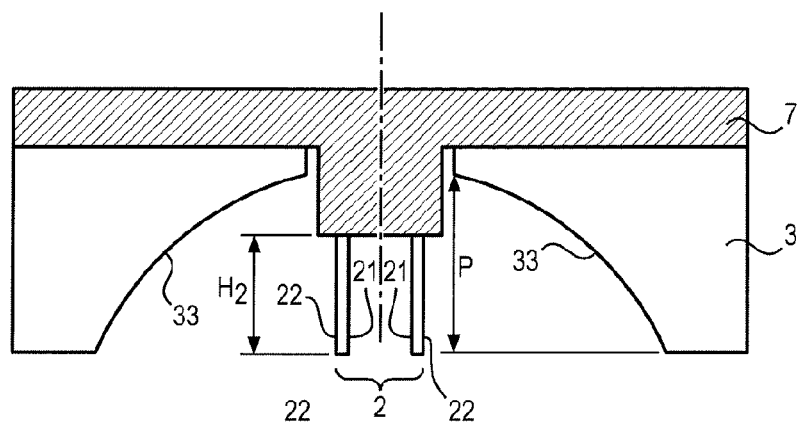
Figure 3B:
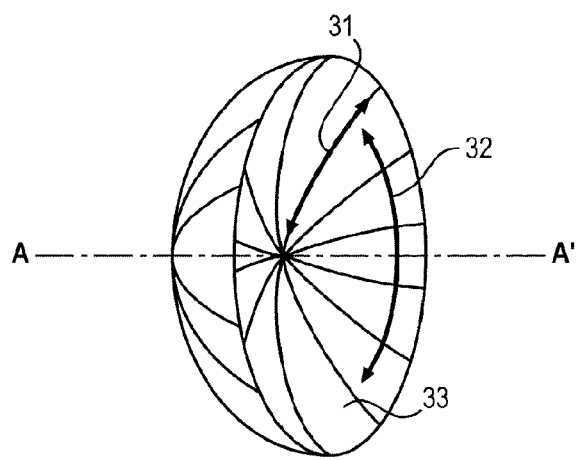

With reference to FIG. 3 an illustration is given of a first embodiment of the device according to the invention.

The device comprises the ring 1 previously described, means 2 for generating ultrasound and a reflector 3.

The ultrasound generating means 2 consist of a tubular transducer in a single block. The transducer comprises an inner electrode 21 forming a rear side of the tubular transducer (i.e. the inner side of the tube) and an outer electrode 22 that is earthed forming a front side of the tubular transducer (i.e. the outer side of the tube) radiating the generated ultrasound waves. In the embodiment illustrated in FIG. 3 the transducer has a diameter of 5 millimetres and a height of 10 millimetres.

The reflector 3 is in the form of a dome pierced at its apex. It has two radii of curvature:

a first so-called meridional radius of curvature 31 passing through the axis of revolution A-A' of the dome 1; and a second so-called sagittal radius of curvature 32 parallel to the axis of revolution A-A' of the dome.

The inner concave side 33 of the dome 3 forms an active face allowing the reflection of the ultrasound waves generated by the tubular transducer 2. The dimensions of the reflector are designed to be sufficient to allow the positioning of the transducer 2 in the centre of the reflector 3. In particular, the depth P of the dome is equal to or greater than the height H of the transducer 2.

The reflector 3 and the transducer 2 are fixed onto a support 7 consisting of a ring-shaped support. Advantageously, the outer diameter of the support 7 is equal to or larger than the inner diameter of the distal end 12 of the ring 1 to allow the positioning of the support 7 on the distal end 12 of the ring 1. The reflector 3 can be integrated in the support 7 so that the support 7 and the reflector 3 are formed of one same piece. As a variant, the reflector 3 and the support 7 can be in several parts.

The transducer 2 and the reflector 3 are positioned on the support so that their respective axes of revolution are coaxial. The transducer 2 is positioned in the centre of the reflector 3. In other words, the effective portion of the active face 33 of the reflector 3 surrounds the tubular transducer 2.

The operating principle of the device illustrated in FIG. 3 is as follows. The user positions the ring 1 over the patient's eye 4. Once the ring 1 is centred on the eye 4, the user actuates the suction device 5. The user then positions the support 7 comprising the ultrasound generating means 2 and the reflector 3 on the ring 1.

The user then sets in operation the generation of ultrasound to burn the ciliary body 41. The front face 22 of the transducer 2 radiates the ultrasound waves which propagate radially relative to the reflector 3. The ultrasound waves come into contact with the active face 33 of the reflector 3. The ultrasound waves are reflected by the latter and are focused in the region of the ciliary body 41 of the eye 4.

The use of a tubular transducer provides for facilitated manufacture of the device to treat an ocular pathology, this type of transducer being sturdy and easy to bond and weld. In addition this device allows a circular lesion to be formed around the entire circumference of the ciliary body 41 and thereby treats the entire ciliary Body 41 using a single activation.

Prototype 2

Figure 4:
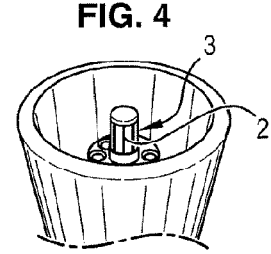

With reference to FIG. 4 an illustration is given of a variant of embodiment of the device illustrated in FIG. 3. This device comprises the same ring 1 and the same reflector 3 as those described with reference to FIG. 3.

The device illustrated in FIG. 4 differs from the device in FIG. 3 in that the ultrasound generating means 2 comprise eight transducers. Each transducer is in the form of portions of a cylinder of width 2 millimetres and height of 6 millimetres. These transducers are arranged in relation to one another to form a tubular assembly.

This tubular assembly of transducers can be obtained for example by dividing into sectors the one-piece transducer illustrated in FIG. 3. The sectoring method may consist of sectioning the outer electrode of the tubular one-piece transducer parallel to its axis of revolution.

With this device it is possible to create a plurality of lesions in the form of a portion of a circle on the ciliary body.

Modelling of Prototypes 1 and 2

Figure 5:
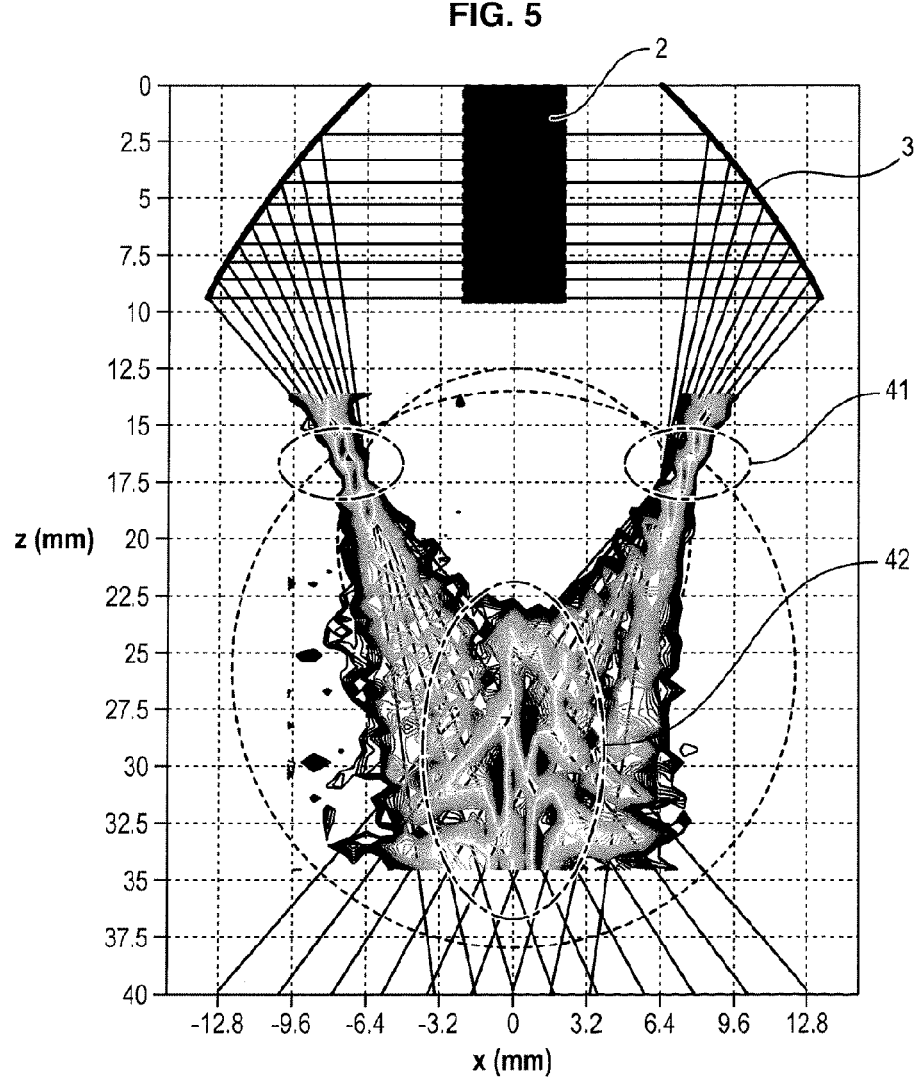
FIG. 5 schematically illustrates modelling of the devices in FIGS. 3 and 4.

FIG. 5 schematically illustrates modelling of the devices in FIGS. 3 and 4. As can be seen, the device allows the obtaining of two focusing areas:
- a first focusing area 41 in a region of the ciliary body due to the meridional radius of curvature;
- a second focusing area 42 in a region of the vitreous humour due to the sagittal radius of curvature.

So as not to cause adverse effects in the area 42 of the fundus of the eye:
- the duration and power of the ultrasound generated by the tubular transducer 2 of the device illustrated in FIG. 3 are chosen to be sufficiently low to avoid excessive heating at the second focusing area 42;
- the transducers of the device illustrated in FIG. 4 are activated in succession to avoid excessive heating at the second focusing area 42.

Prototype 3

Figure 6:
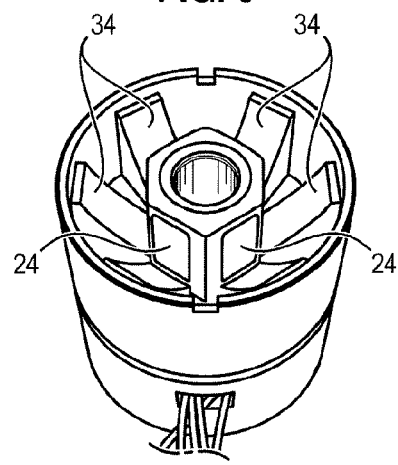

With reference to FIG. 6 an illustration is given of another embodiment of the device for treating an ocular pathology.

In this embodiment the ultrasound generating means 2 comprise six planar rectangular transducers 24. The use of planar transducers 24 provides an advantage in terms of handling, easy manufacture and hence cost.

These transducers 24 are positioned in relation to one another so as to form an alveolus of hexagonal cross-section.

The device also comprises six reflectors 34 having the form of a cylinder portion. These reflectors 34 surround the ultrasound generating means 2. Each reflector 34 is associated with a respective planar transducer 24, the active face 33 of the reflector 34 lying opposite the front face 22 of its associated transducer 24.

The device illustrated in FIG. 6 allows six linear lesions to be formed on the ciliary body 41.

The presence of a plurality of reflectors 34 in the form of a cylinder portion allows a set of reflectors 34 to be obtained having a single meridional radius of curvature 31.

The omission of the sagittal radius of curvature 32 thus obtained avoids the need for the second focusing area 42 with the devices illustrated in FIGS. 3 and 4.

Prototype 4

Figure 7:
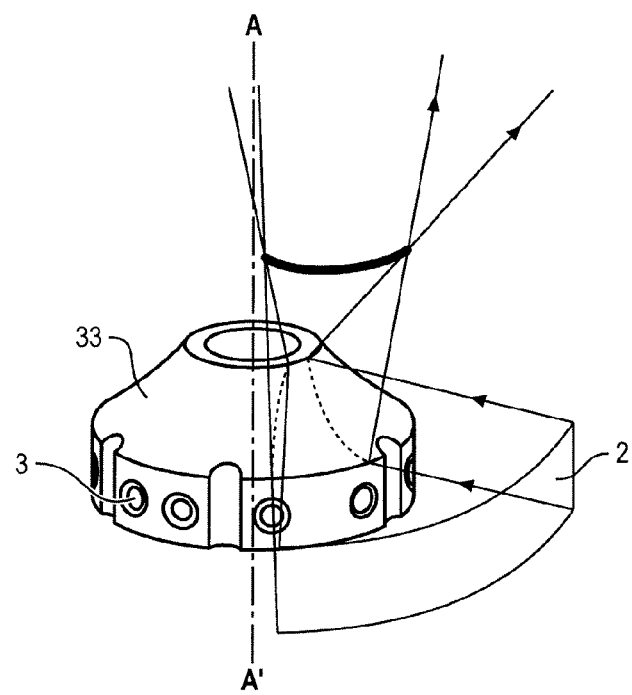

With reference to FIG. 7 another embodiment is illustrated which firstly allows limiting of the volume of the device illustrated in FIG. 5 and secondly allows circular lesions to be obtained on the ciliary body 41.

In this embodiment, the ultrasound generating means 2 surround the reflector 3.

The ultrasound generating means 2 are ring-shaped. They may be formed of a single annular transducer or of several transducers in the form of a cylinder portion arranged in relation to one another so as to form an annular assembly. In either case, the ultrasound generating means 2 are arranged to generate ultrasound waves propagating radially in the direction of the axis of revolution of said ultrasound generating means. For example, for the ultrasound generating means formed of a single annular transducer, the inner side thereof is intended to radiate the generated ultrasound waves, the outer side being connected to the hot point.

The active face 33 of the reflector 3 is in the form of a concave truncated cone. The reflector 3 therefore has two radii of curvature: a meridional radius of curvature 31 related to the concavity of the reflector 3 and a sagittal radius of curvature 32 related to the symmetry of revolution of the reflector 3.

The operating principle of this device is as follows. The transducer(s) 2 generate ultrasound waves which converge towards the axis of revolution A-A' of the transducer(s) 2. The ultrasound waves come into contact with the reflector 3. The active face 33 of the reflector 3 reflects the ultrasound waves in the direction of the eye 4 of the patient to be treated. The ultrasound waves propagate and are focused in the area of the ciliary body 41 of the patient's eye 4 on account of the meridional radius of curvature 31. After being focused on the ciliary body 41, the reflected beam continues to propagate towards outside the eye 4 and is focused a second time outside the eye.

The flared truncated cone shape—or concave truncated cone—of the reflector therefore leads to two focuses: first focusing on the ciliary body 41 and second focusing outside the eye 4. Unlike the embodiments illustrated in FIGS. 3 and 4, the second focusing lies outside the eye on account of the shapes and arrangement of the reflector 3 and of the ultrasound generating means 2.

Persons skilled in the art will appreciate that numerous modifications can be made to the above-described device without departing in substance from the novel teachings herein.

For example in the above-described embodiments, the shape of the reflector is adapted for focusing of the ultrasound waves, in particular through the concave shape of the active face of the reflector. As a variant, the shape of the reflector can be adapted to defocus the ultrasound waves so as to irradiate a larger tissue area without focusing, in particular by means of a concave shape of the reflector.

The examples given in the foregoing are evidently particular illustrations only and in no way limiting.

The invention claimed is:

1. A device for treating an ocular pathology, comprising a ring having a proximal end intended to be in contact with a patient's eye and a distal end intended to receive ultrasound generating means wherein the device further comprises at least one reflector having an active concave face facing the ultrasound generating means to reflect and focus the ultrasound waves generated by the generating means in a region of the patient's eye.

2. The device according to claim 1, wherein the ultrasound generating means comprises at least one transducer having a front side to radiate the ultrasound waves, the front side of each transducer extending parallel to the axis of revolution of the ring.

3. The device according to claim 1, wherein the ultrasound generating means comprises a single tubular transducer.

4. The device according to claim 1, wherein the ultrasound generating means comprises a plurality of transducers, said transducers being positioned on generating lines of a tube.

5. The device according to claim 4, wherein each transducer is in the form of a cylinder portion.

6. The device according to claim 4, wherein each transducer is planar.

7. The device according to claim 1, which further comprises a support for supporting the ultrasound generating means and each reflector, the ultrasound generating means being positioned in a central region of the support and each reflector being positioned in a peripheral region of the support.

8. The device according to claim 1, wherein the reflector comprises an active concave toroid face.

9. The device according to claim 1, wherein the reflector comprises a plurality of reflecting elements, each reflecting element comprising an active face in the form of a cylinder portion.

10. The device according to claim 7, which further comprises a support for supporting the ultrasound generating means and each reflector, the ultrasound generating means being positioned in a peripheral region of the support and each reflector being positioned in a central region of the support.

11. The device according to claim 10, wherein the reflector comprises an active face in the form of a truncated cone, said truncated cone being concave or planar or convex.

12. The device according to claim 1, wherein the ultrasound generating means is of tubular shape and the reflector is of truncated cone shape, said truncated cone shape being concave, planar or convex, the diameter of the ultrasound generating means being larger than the diameter of the reflector, the ultrasound generating means and the reflector being arranged so that:
  axes of revolution of the reflector and of the ultrasound generating means merge;
  the ultrasound generating means surrounds the reflector;
  an inner side of the ultrasound generating means radiating ultrasound waves faces an active face of the reflector.

* * * * *

UNITED STATES PATENT AND TRADEMARK OFFICE
CERTIFICATE OF CORRECTION

PATENT NO. : 8,905,949 B2  
APPLICATION NO. : 14/009622  
DATED : December 9, 2014  
INVENTOR(S) : Fabrizio Romano et al.

Page 1 of 1

It is certified that error appears in the above-identified patent and that said Letters Patent is hereby corrected as shown below:

Title Page, item (73) Assignees should be changed from "Eye Tech Care, Rillieux-La-Pape (FR)" to --Eye Tech Care, Rillieux-La-Pape (FR) and Institut National de la Sante et de la Recherche Medicale (INSERM), Paris (FR)--.

Signed and Sealed this  
Fifteenth Day of September, 2015

Michelle K. Lee  
*Director of the United States Patent and Trademark Office*